United States Patent [19]

Schnipelsky et al.

[11] 4,257,862
[45] Mar. 24, 1981

[54] CHEMICAL ANALYZER

[75] Inventors: Paul N. Schnipelsky, Rochester; Raymond F. Jakubowicz, Canandaigua, both of N.Y.

[73] Assignee: Eastman Kodak Company, Rochester, N.Y.

[21] Appl. No.: 927,702

[22] Filed: Jul. 24, 1978

[51] Int. Cl.³ .......................................... G01N 27/28
[52] U.S. Cl. ........................... 204/195 R; 204/195 B; 422/63; 422/67; 422/98
[58] Field of Search ............... 204/195 R, 195 B; 364/416, 497; 422/65, 98, 66, 67, 63, 64; 324/29; 195/127; 73/1 R

[56] References Cited

U.S. PATENT DOCUMENTS

| | | | |
|---|---|---|---|
| 2,904,914 | 9/1959 | Trubert | 40/78 |
| 3,161,323 | 12/1964 | Bent | 222/41 |
| 3,260,413 | 7/1966 | Natelson | 422/66 X |
| 3,502,560 | 3/1970 | Wise | 204/195 |
| 3,544,272 | 12/1970 | Vaills | 23/253 |
| 3,575,834 | 4/1971 | Hoole et al. | 204/195 |
| 3,604,815 | 9/1971 | Clemens | 356/191 |
| 3,735,902 | 5/1973 | Zindler | 222/363 |
| 3,798,431 | 3/1974 | Schulkind et al. | 364/497 X |
| 3,837,534 | 9/1974 | Natelson | 222/137 |
| 3,874,850 | 4/1975 | Sorenson et al. | 204/195 B X |
| 3,923,399 | 12/1975 | Brumley | 356/96 |
| 3,941,487 | 3/1976 | Ehret et al. | 356/181 |
| 3,975,727 | 8/1976 | Mader et al. | 73/1 R X |
| 4,053,381 | 10/1977 | Hamblen et al. | 204/195 M |
| 4,054,415 | 10/1977 | Seligson et al. | 23/253 R |
| 4,058,367 | 11/1977 | Gilford | 23/253 R |
| 4,110,167 | 8/1978 | Melnyk | 195/127 |
| 4,152,390 | 5/1979 | Nosco et al. | 422/63 |

Primary Examiner—G. L. Kaplan
Attorney, Agent, or Firm—D. D. Schaper

[57] ABSTRACT

A method and apparatus are disclosed for performing chemical analysis on selected fluids. The fluids are dispensed onto a test element which is transported to an analysis device where a radiometer or potentiometer is provided for measuring a characteristic of the test element resulting from the fluid deposited thereon.

4 Claims, 13 Drawing Figures

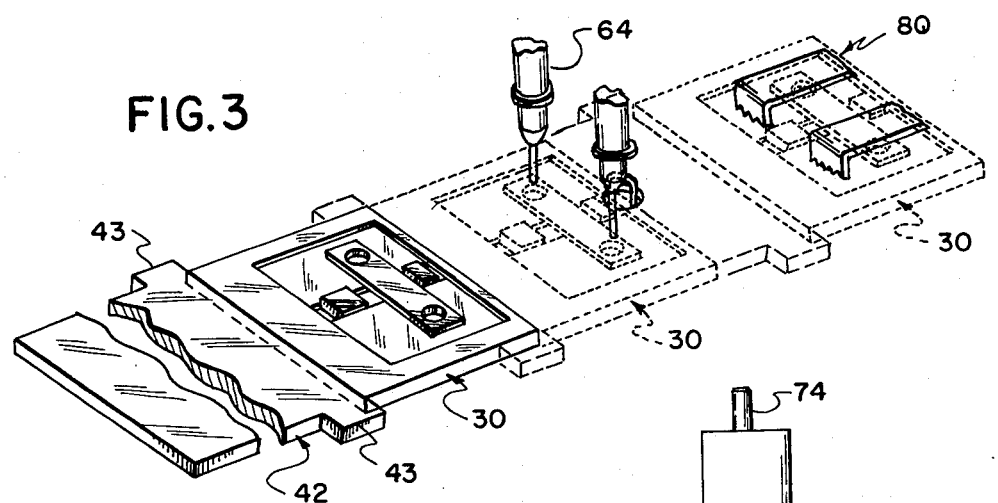
FIG. 3
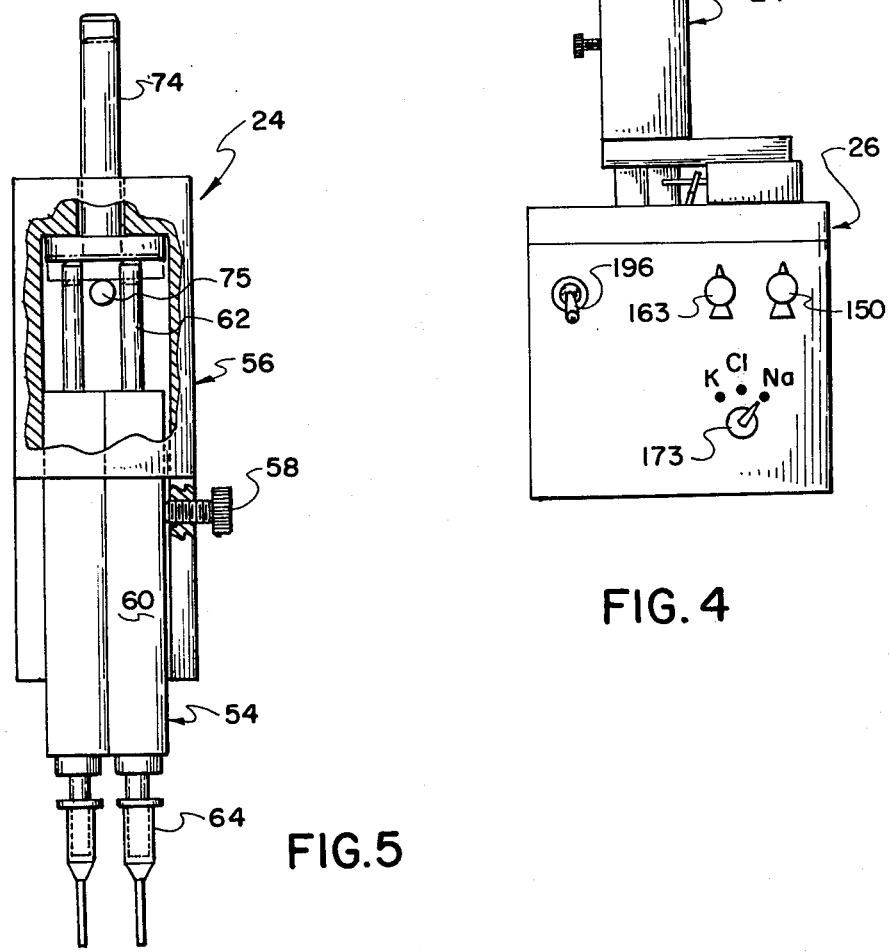
FIG. 4
FIG. 5

CHEMICAL ANALYZER

CROSS-REFERENCES TO RELATED APPLICATIONS

Reference is made to commonly-assigned U.S. Patent Applications: Ser. No. 818,255, entitled CONTINUOUS-MONITORING MULTICHANNEL ANALYZER, filed in the name of Schnipelsky et al., on July 22, 1977, now abandoned; Ser. No. 893,656, entitled ION SELECTIVE ELECTRODE, filed in the name of C. Battaglia et al., on Apr. 5, 1978 now abandoned, and Ser. No. 856,834, entitled CHEMICAL ANALYZER, filed in the name of Nosco et al., on Dec. 2, 1977, and now U.S. Pat. No. 4,152,390

BACKGROUND OF THE INVENTION

1. Field of the Invention

This invention relates to the chemical analysis of substances, and more particularly, to a method and apparatus for the potentiometric or radiometric analysis of a test element having a biological fluid deposited thereon.

2. State of the Prior Art

Chemical analyzers have been developed for performing quantitative chemical analyses of biological fluids, such as blood serum, to enable the physician to obtain a more complete picture of a person's physical condition. In one type of such apparatus, reagents are added to a sample of blood serum, and after sufficient incubation, a color change or a fluorescence is sensed by a radiometer. In a second type of apparatus, certain ionic blood components are detected potentiometrically by measuring the potentials generated by ion-selective electrodes (hereinafter referred to as ISE's). Included in such tests are the ions $Cl^\ominus$, $Na^\oplus$, $K^\oplus$ and $HCO_3^\ominus$.

Apparatus for measuring various ions in solution typically include a reference electrode and an ISE which incorporates a reference half-cell, generally comprising a solution of known ion activity. When the reference electrode and the ISE are immersed in a solution to be analyzed, an electrochemical cell is formed and a potential developes across the electrodes of the cell. This potential is proportional to the logarithm of the activity of ions in solution to which the ISE is sensitive. The logarithmic relation is described by the well-known Nernst equation.

Most of the commercially-available apparatus for testing the electrolyte concentrations in a biological fluid utilize liquid reagents and require analyzer equipment having intricate solution handling and transport capabilities. Such apparatus is complex and expensive, requires skilled operators, and must be used in a laboratory setting where suitable power and plumbing facilities are available. Further, known prior-art devices normally require large amounts of the sample fluid to be tested, since they utilize relatively large, bulky electrodes which must be immersed in the sample fluid. Electrodes of the type described are disclosed in U.S. Pat. No. 3,502,560 to Wise, issued Mar. 24, 1970, and U.S. Pat. No. 3,575,834, to Hoole et al., issued Apr. 20, 1971.

The measuring of electrolyte concentrations in blood serum is an important tool in certain clinical analyses which must be performed under emergency conditions. For example, the concentration of sodium ions in the blood can be an indication of dehydration, and an elevated potassium concentration can indicate a weak cardiac muscle which can stop at any time. Thus, a need has existed for a portable, compact analyzer which is adapted to perform emergency tests in a variety of locations, such as in an ambulance, in an operating room, or in the physician's office or clinic. None of the prior-art devices, which require complex solution handling devices and use large bulky electrodes, are suitable for such use.

Recent developments have provided ISE's in essentially planar, dried form, suitable for use in pairs in an analyzer. An example of such a device is described and claimed in commonly-owned U.S. Pat. No. 4,053,381, issued Oct. 11, 1977, entitled "Device for Determining Ionic Activity of Components of Liquid Drops."

OBJECTS OF THE INVENTION

It is an object of the present invention to overcome the above-described problems of prior-art devices, and to provide a simple, efficient method and apparatus for performing radiometric and potentiometric analysis under emergency conditions, as well as in a laboratory setting.

Another object of the present invention is to provide a portable, compact analyzer to measure the potentiometer or radiometric response of a multi-layer analytical electrode or element and to report the response in units of analyte concentration.

Yet another object of the invention is to provide chemical apparatus for the analysis of biological fluids wherein dispensing means are mounted on the apparatus such that fluids can be aspirated from a supply remote from a metering position on the apparatus and dispensed from the metering position.

A further object of the invention is to provide chemical apparatus of the type described wherein a plurality of operations are performed on a test element advanced along a stationary support means.

A still further object of the invention is to provide a method and apparatus for calibrating a chemical analyzer in which no calibrating fluids are required.

Other objects and advantages will become apparent from the following summary and description of the preferred embodiments, when considered in light of the attached drawings.

SUMMARY OF THE INVENTION

The present invention relates to a method and apparatus for determining the concentration of certain analytes in biological fluids. In a preferred embodiment of the apparatus, predetermined amounts of sample fluid and of reference fluid are metered onto a test element which comprises a pair of ion-selective electrodes. After a fixed period of time, an analysis device measures the potential generated across the electrodes, which is indicative of the concentration of ions in the fluid.

More specifically, in accordance with one aspect of the invention, apparatus is provided for chemical analysis of a sample fliud wherein a plurality of operations are performed in sequence on a test element adapted to receive said fluid and to produce a response indicative of a characteristic of the fluid, said apparatus comprising: stationary support means for receiving a test element from a supply thereof and providing continuous support for the element during each of said operations; metering means for supplying a quantity of sample fluid to a test element located at a metering position on said support means, said metering means being disposed adjacent said support means; analysis means for measuring a response from a test element bearing said quantity of fluid and supported at a sensing position on said support means, said analysis means being operable a preselected time after said fluid has been supplied to the test element; and transfer means mounted on said support means and moveable therein for sequentially advancing an element from said metering position to said sensing position and for effecting the removal of said element from the sensing position after said response has been measured.

In one embodiment of the invention, the metering means comprises a pair of dispensing means which are movable between a source of fluids and a location on the analyzer where sample and reference fluids are delivered to a test element containing a pair of ion selective electrodes. The dispensing means are disclosed as syringes which are removably mounted on the analyzer and have a common actuating means. The actuating means is adapted to compensate for different plunger heights in the syringes.

The analysis means comprises an electrometer having a pair of contacts movable into electrical connection with the electrodes in the test element and a means for processing a signal from the electrometer to convert the signal into units of analyte concentration. The analyzer is calibrated by electronic means, and thus, there is no necessity for using calibrator fluids.

BRIEF DESCRIPTION OF THE DRAWINGS

FIG. 3 is a perspective view showing the relative positions of the transfer mechanism and the test element when the test element is in the receiving, metering and sensing positions;

FIG. 4 is a rear elevational view of the analyzer;

FIG. 5 is a elevational view of one embodiment of the metering device, with parts broken away to show the actuating mechanism;

DESCRIPTION OF THE PREFERRED EMBODIMENTS

The invention is described hereinafter in connection with a potentiometric analyzer for use with ion-selective electrodes. However, the invention is not so limited, and it can also be employed in an analyzer using a radiometric detector which will read any suitable substrate incorporating, for example, reagents that create a dye in proportion to the analyte being measured. Such reagents can be in solution or in the form of a dried coating.

In the case of potentiometric analyzers, the substrate which makes the test possible comprises a pair of electrodes selective to the ion activity of choice, hence the name ion-selective electrode, or ISE. Such electrodes, by the use of a salt bridge, permit the generation of an electrical signal, in the presence of the sample test liquid, that is indicative of the test ion activity and thus the concentration. As used herein, "response" not otherwise limited includes an electrical signal derived from paired electrodes, and also includes any detectable response to the substrate that is indicative of the level of analyte of choice. Thus, "response," except where limited, is used in the broadest sense to include both potentiometric and radiometric detection.

Figure 1:
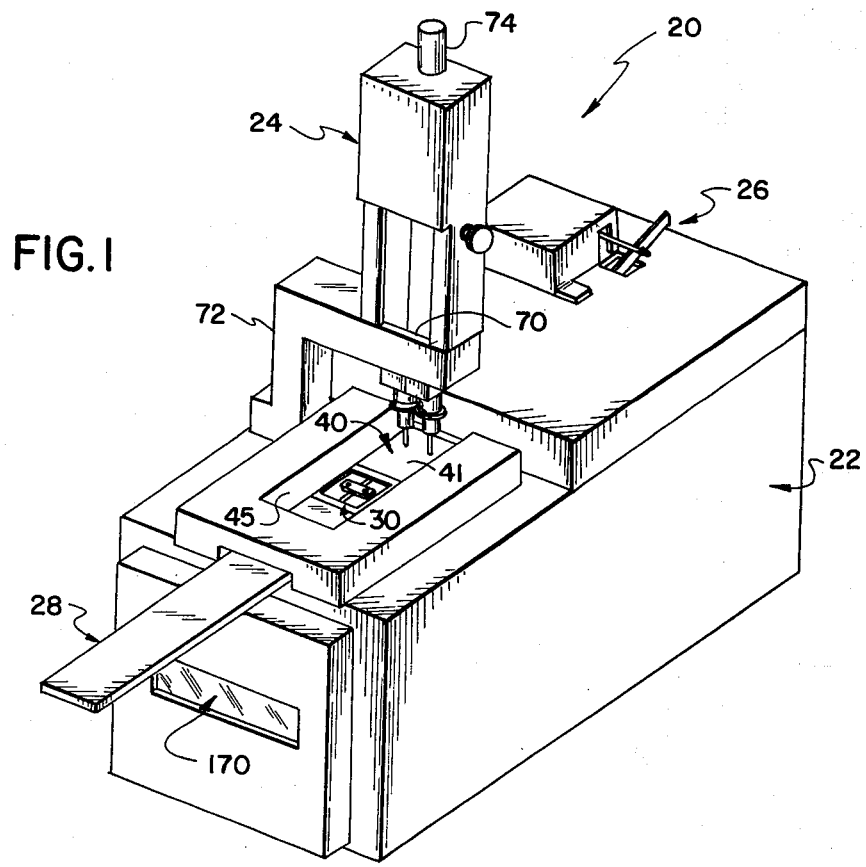
FIG. 1 is a perspective view of an analyzer constructed in accordance with the invention.

In accordance with a preferred embodiment of the invention, there is shown in FIG. 1 a chemical analyzer 20 comprising a housing 22, a metering device 24 supported on the housing, an analysis device 26, and a transfer mechanism 28. As will be discussed in more detail hereinafter, analyzer 20 is adapted to receive a test element 30, in the position shown in FIG. 1 at a forward end of the analyzer, to support the element as it is moved rearwardly into a metering position where reference fluid and sample fluid are deposited on the element, and then to sense a potential developed in the element after it has been moved into the analysis device.

Figure 2:
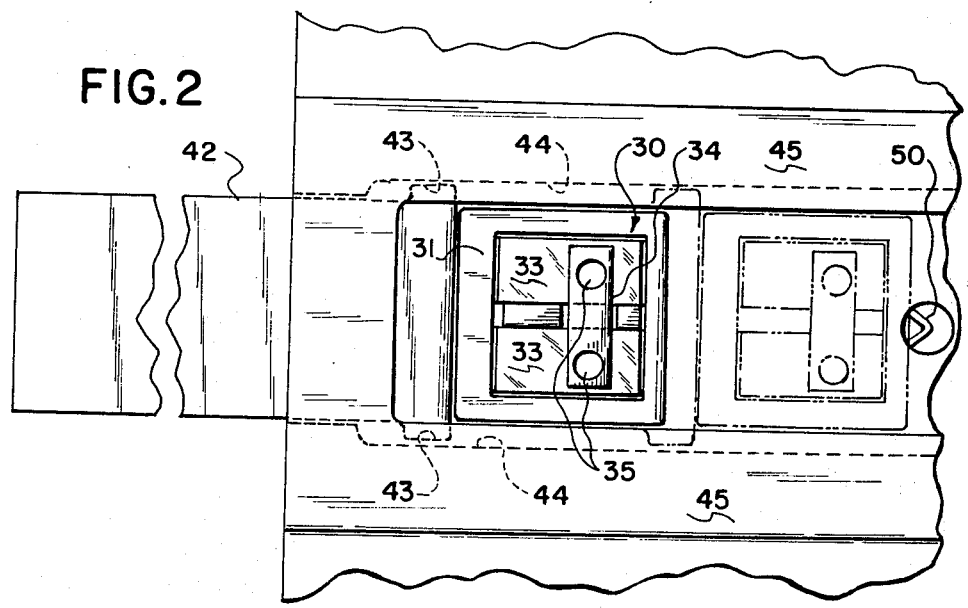
FIG. 2 is a fragmentary top plan view showing a test element in solid lines in a receiving position on the analyzer track means, and in phantom in the metering position.

Any generally planar form of ISE can be used in the test element, preferably in pairs to permit a differential measurement to be made comparing the ion activity of an unknown sample fluid with the known ion activity of a reference fluid. One convenient type of test element, illustrated as a slide, is that disclosed in the aforesaid commonly-assigned U.S. Pat. No. 4,053,381, to Hamblen et al., the disclosure of which is expressly incorporated herein by reference. Test element 30, as shown in FIG. 2, comprises a frame 31 which is adapted to support a pair of ISE's 33 having a generally planar strip form, and a bridge 34 used to promote ionic migration between the reference fluid and the sample fluid deposited over the electrodes. Apertures 35 are provided in bridge 34 to insure the appropriate contact of the sample fluid and reference fluid with the ISE's. Silver chloride coated surfaces of the ISE's are exposed for the purpose of making readings as hereinafter described.

With reference to FIGS. 1 and 2, analyzer 20 includes stationary support means in the form of a track 40 which is fixed to housing 22. Track 40 comprises side walls 45 which serve to locate the test element in a direction transverse to the direction of test element movement, and a floor 41 which provides a generally flat continuous bearing surface for supporting the test element 30 during the entire test procedure. Mounted for slidable movement within track 40 is a transfer mechanism 28. Mechanism 28 comprises an elongate member 42 having a pair of tabs 43 at one end thereof which are received in guide means in the form of grooves 44 in walls 45. (See FIG. 6.) Thus, at the start of a test, an operator would place a test element 30 in a receiving position on a forward portion of the track 40, shown in solid lines in FIG. 2, and advance the element by means of member 42 into a metering position, shown in phantom in FIG. 2. A spring-biased stop 50 in track means 40 acts as an abutment to stop test element 30 in the metering position, thereby locating the element relative to metering device 24. With test element 30 in the metering position, metering device 24 is actuated to substantially simultaneously deposit a sample fluid and a reference fluid in apertures 35 of the test element.

With reference to FIG. 5, metering device 24 comprises a pair of dispensing means, shown as syringes 54, which are removably mounted in a holder 56 and are held therein by means of a threaded element 58. Each of the syringes 54 comprises a barrel 60, a plunger 62 movable within the barrel, and a removable tip 64 which serves as a fluid storage means, or reservoir, for the fluid. Syringes 54 are filled by first placing tip 64 in a fluid and moving plunger 62 downwardly a sufficient distance to displace a volume in barrel 60 slightly in excess of the volume of fluid required for one test element; the plunger is then released to permit an internal spring, not shown, to return the plunger to its uppermost position, thereby aspirating the desired volume of fluid into the syringe. Fluid is drawn only into tip 64; thus, barrel 60 does not become contaminated, and only the tip 64 must be replaced when a new fluid is introduced. Metering device 24 is removably mounted in an opening 70 (FIG. 1) in a mounting bracket 72 on housing 22. A T-bar 74 is slidably mounted in holder 56 and is adapted to simultaneously actuate plungers 62 in the two syringes to expel fluid from tips 64 onto a test element. A stop 75 limits downward movement of T-bar 74 to insure that a precise amount of fluid will be metered from tips 64. Only micro-amounts of fluid are metered onto test element 30; for example, in a typical operation 10 $\mu$l of reference fluid and 10 $\mu$l of sample fluid are sufficient to perform a test. When metering device 24 is in position on analyzer 20, tips 64 are closely adjacent element 30 such that the fluids bridge the gap between tip 64 and the element 30 during the metering operation.

Figure 6:
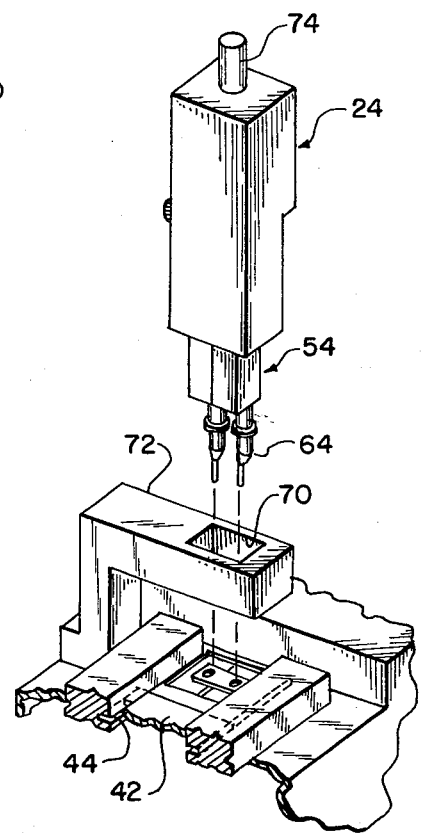
FIG. 6 is a perspective view of the metering device, with the syringes in a reversed position to accommodate a reversed polarity in the ion being tested.

As shown in FIG. 6, a simple means is provided for accommodating a different polarity in the ion being tested. This is accomplished by rotating the device 24 by 180 degrees, from its position in FIG. 1, to reverse the positions of the two syringes and thereby reverse the positions from which sample fluid and reference fluid are dispensed from device 24.

Figure 13:
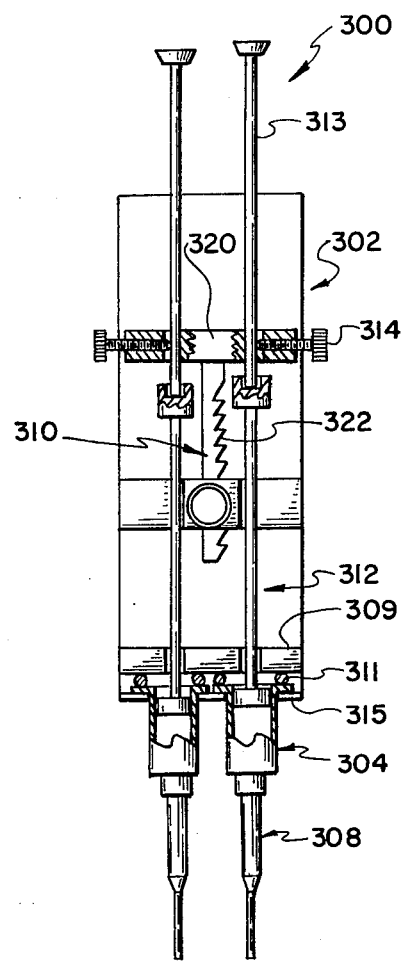
FIG. 13 is an elevational view of a second embodiment of a metering device for use in the disclosed analyzer, with portions of certain elements shown in section.

A second embodiment of a metering device for use with analyzer 20 is shown in FIG. 13. With reference to FIG. 13, there is shown a metering device 300 which comprises a body member 302 having mounted thereon one syringe 304 which is adapted to contain reference fluid and another syringe 304 which is adapted to receive sample fluid. Each of the syringes 304 contains a plunger 312 which is operable in a well-known manner to draw fluid into the syringe through a metering tip 308 and to dispense fluid therefrom. Syringes 304 are removably mounted between flanges 309, 315, on body member 302 and are held therein by resilient elements 311.

Device 300 can be used to deposit fluids on a number of test elements, without recharging the syringes. A plunger actuating means 310 is adapted to index plungers 312 by precise increments to successively dispense a plurality of drops. The syringe containing sample fluid is not normally used to dispense more than four drops (one for each ion being tested) before refilling with a new sample fluid, whereas the syringe containing reference fluid can be used for a much greater number of drops. Thus, the two plungers 312 are frequently at different heights relative to each other and to the actuating means 310. Actuating means 310 includes a means for compensating for the different plunger heights which includes a block 320 connected to a ratchet mechanism 322 for moving the block in a vertical direction. A pair of pins 313 are slidably received in block 320 and can be fixed in a selected position therein by screws 314. When a syringe 304 is placed on device 300, a pin 313 is brought into contact with plunger 312 and a screw 314 is tightened to hold the pin in place; thus it will be seen that each of the plungers will be moved the same amount with each actuation of ratchet mechanism 322 regardless of the respective positions of the two plungers 312. Device 300 can be mounted in opening 70 in bracket 72 and used in the same manner as described above for device 24.

After the fluids have been deposited on test element 30, the element is moved into analysis device 26 by transfer mechanism 28. In an element 30 is in the analysis device 26 when a new element 30 is being moved in, the new element serves to push the old element out of device 26 and into a disposal receptacle, not shown.

Figure 7:
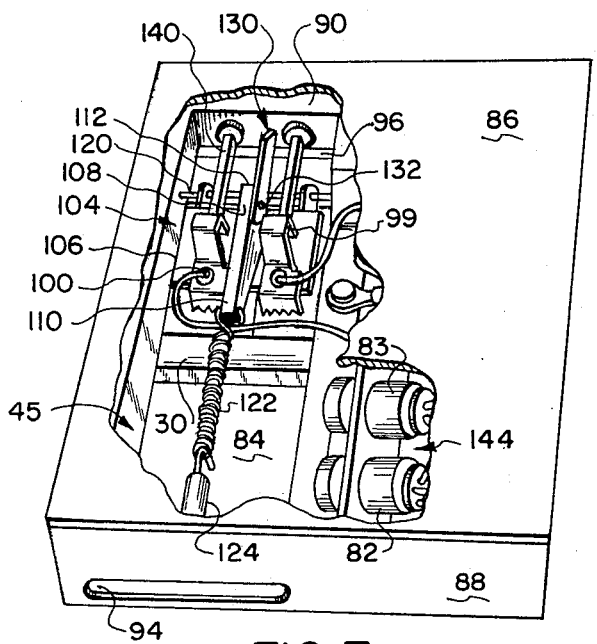
FIG. 7 is a perspective view of the analysis device incorporated in the analyzer.

As best shown in FIG. 7, analysis device 26 comprises contacts or probes 80, one for each ISE, and an electrometer 144 wired to the probes 80 and connected to a circuit board, not shown, which includes means for processing the signal from electrometer 144. (See FIGS. 9–11.) Electrometer 144 includes a pair of operational amplifiers 82 and 83. Analysis device 26 is formed by a bottom wall 84 which serves as a part of track floor 41, a cover plate 86 which is preferably removably mounted by fasteners, not shown, front wall 88, and rear wall 90. The probes 80 are disposed to project into the path of an element 30 which is moved into the analysis device through an entrance slot 94 and is ejected through an exit slot 96. A spring biased stop, not shown, similar to stop 50, projects through bottom wall 84 and serves to position element 30 relative to probes 80. Probes 80 are generally Z-shaped with spaced teeth or serrations 98 at one end and stop flanges 99 at the other. The probes 80 are held in place by screws 100 on a pivot member 104. Member 104 in turn comprises a base 106 and a central, upstanding shoulder 108 perforated at front portion 110 and rear portion 112. Base 106 is journaled to side walls 45 by means of a pivot pin 120 at a distance sufficiently spaced above bottom wall 84 to accommodate element 30.

Figure 8:
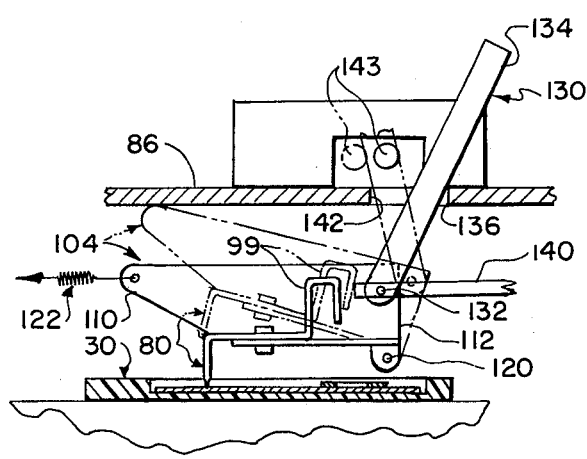
FIG. 8 is a fragmentary elevational view of the electrometer contacts and the contact lifting mechanism.

To bias pivot member 104 downwardly against a test element in the sensing position, as shown in FIG. 8, a bias or tension spring 122 is secured at one end to front portion 110 and at its opposite end to a link 124 attached to front wall 88 of the device. The spring 122 is selected to be of a strength sufficient to rotate member 104 about pivot pin 120 and to force teeth 98 through an exposed nonconductive silver chloride coating on the test element and into contact with a conductive silver layer below the silver chloride. By such means, probes 80 are constantly in contact with the electrodes of test element 30 to provide a continuous readout.

To raise probes 80 during loading and unloading of the slides, a release arm 130 is pinned at 132 to portion 112 of the pivot member 104. (See FIG. 8.) The opposite end 134 of arm 130 projects through opening 136 in cover plate 86 and is of a length sufficient to permit the operator to grasp the end 134 for raising the probes. Stop rods 140 are attached to rear wall 90 and limit movement of the probes as they are pivoted away from the track floor 41. As shown in FIG. 8, arm 130 abuts against a portion 142 on cover plate 86 to effect the raising of probes 80. As arm 130 moves forward, it actuates a switch 143 which starts a timer 182 (FIG. 11) for measuring the incubation period necessary for a reaction occurring in element 30 to reach a stable potential.

Although an incubation period is necessary for the reaction in the test element to stabilize, the disclosed analyzer does not require temperature control means to obtain desired precision under most operating conditions. However, under extreme field conditions, it is contemplated that either heated or cooled air could be furnished to analysis device 26, using conventional temperature control devices.

The ability of the analyzer to measure the response of the ISE chips in the differential mode is based on the following Nernstian equation:

$$E_m = \text{slope} \log \frac{\alpha_{sample}}{\alpha_{reference}}$$

wherein:
$E_m$ = potential generated by element 30
slope = slope of curve defined by Nernstian relationship
$\alpha$ = ion activity.

Rearranging and collecting constants, the above equation becomes:

$$\text{Conc}_{sample} = 10 \frac{E_m - K_1}{K_2}.$$

$K_1$ is a constant related to the logarithm of the reference concentration, and $K_2$ is a constant related to the Nernstian slope characteristic of the test element for a particular analyte. The constants are predetermined for each reference fluid and for each type of ISE test element.

Figure 9:
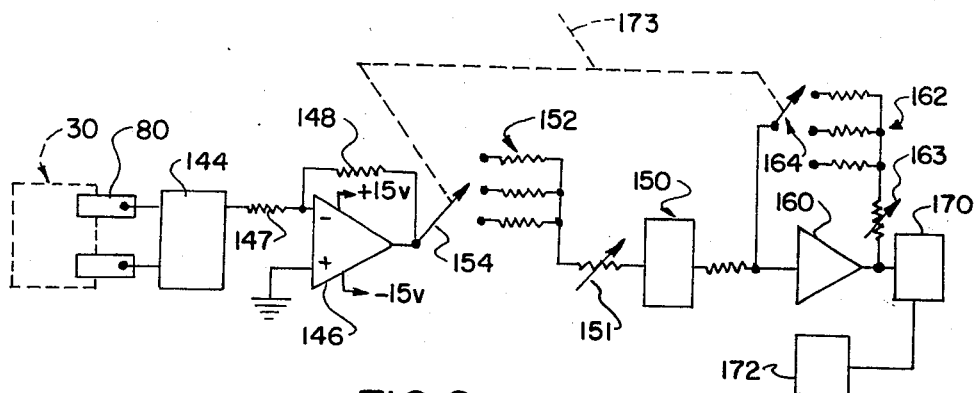
FIG. 9 is a schematic diagram, partially in block form, of an electrical circuit for the analysis device.

With reference to FIG. 9, the potential developed in test element 30 is supplied to electrometer 144 through probes 80. The electrometer preferably is a low drift, high input impedance device having an impedance considerably higher than that of the electrodes. Electrometer 144 comprises an amplifier 83 (FIG. 7) which senses the potential developed in test element 30, and a second amplifier 82 which amplifies the signal from amplifier 83 for further processing. The output from electrometer 144 is coupled to a buffer amplifier 146 through a resistor 147. A resistor 148 in the feedback circuit of amplifier 146 is of a size equal to resistor 147 to produce a unity gain in amplifier 146. The signal developed by amplifier 146 is coupled through a selected resistor in a bank of resistors 152 to a logarithmic amplifier 150 configured in the antilog mode. A switching element 154 is adapted to place a selected resistor of resistor bank 152 in the circuit, depending on the analyte, and a variable resistor 151 is used to calibrate the analyzer, as will be explained in more detail hereinafter. Amplifier 150 converts the response of the test element into an exponential equivalent (i.e., linear scale rather than logarithmic).

Amplifier 150 is connected to a scaling amplifier 160 which scales the result of amplifier 150 to provide a signal which produces the correct response in concentration units (e.g., mEq/L) on a voltmeter 170. A bank of resistors 162 is positioned such that a selected one of the resistors can be interposed in the feedback circuit of amplifier 160; switching element 164 is adapted to place the selected resistor in the feedback circuit in accordance with the analyte being tested and a variable resistor 163 is provided for fine adjustment. The outut from amplifier 160 is registered on voltmeter 170 which may be of the digital type. Switching elements 154 and 164 are actuated by a common control 173 indicated diagrammatically in FIG. 9 and shown in FIG. 4

Figure 11:
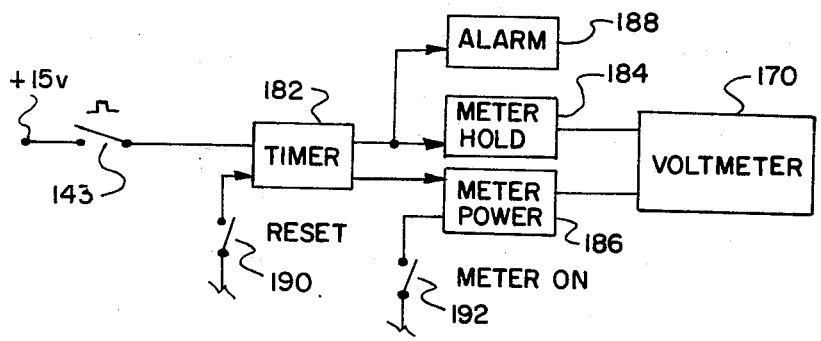
FIG. 11 is a block diagram of the timing circuit used in conjunction with the circuit shown in FIG. 9.

Timing logic, indicated at 172 in FIG. 9 and shown in block form in FIG. 11, is used to obtain and hold a reading on voltmeter 170 after a fixed interval (e.g., 3 minutes after the fluids have been deposited on the test element). With reference to FIG. 11, switch 143 is actuated to supply a pulse to a timer 182 immediately after reference and sample fluids have been deposited on a test element 30. Timer 182 controls the operation of the digital voltmeter 170 by means of logic circuitry designated by block 184 labeled "meter hold," and by logic circuitry designated by block 186 labeled "meter power." To conserve power, the voltmeter 170 is off until a preset time, e.g., 10 seconds, before the actual read and hold operation of the meter is to occur; when this point is reached, a digital pulse from timer 182 effects the application of power to the voltmeter through the "meter power" circuitry. At the completion of the test, a signal from the timer produces the required pulse through the "meter hold" circuitry 184 to hold the final reading of the voltmeter; this pulse also causes the actuation of an audible alarm 188 indicating completion of the test.

A reset switch 190 resets the timer and logic in preparation for the next cycle.

Another switch 192 ("meter on") is adapted to override the delay portion of the circuit so that a continuous display can be observed on the voltmeter.

Figure 10:
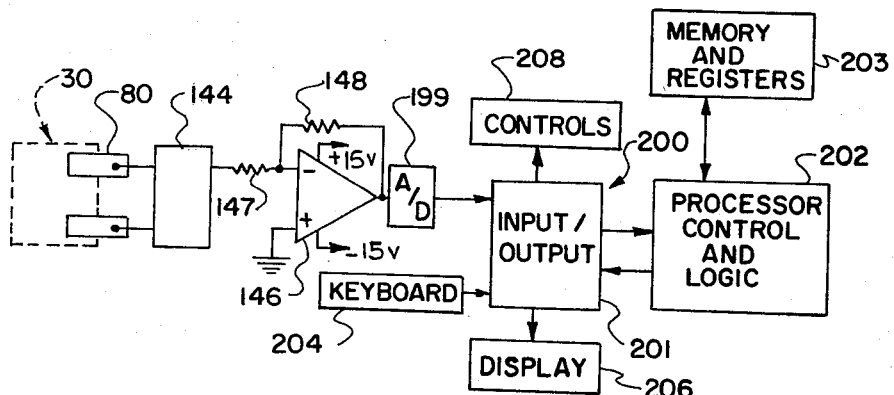
FIG. 10 is a block diagram of an alternate embodiment of an electrical circuit for the analysis device.

A second configuration of the sensing and measuring device includes digital circuitry, as shown in FIG. 10. In the digital embodiment, the signal from buffer amplifier 146 is passed to an analog-to-digital converter 199. The output of the analog-to-digital converter 199 is provided to data translating means, such as a computer 200. The computer may be a commercially-available microcomputer, such as the Motorola M6800 or the Texas Instrument 8080. Computer 200 comprises a standard input/output circuit 201, processor control and logic circuit 202, and memory and register banks 203, all interconnected for processing data at appropriate times. Calibration data for one or more chemistries, as described below, can be provided to computer 200 through a keyboard 204, and stored in registers 203. The data from the converter 199 is collected, and the calculations are performed by computer 200. The result is displayed in concentration units by a display device 206. As indicated at 208 in FIG. 10, computer 200 can be adapted to perform control functions for the apparatus in accordance with programmed instructions stored therein.

Power is preferably supplied to analyzer 20 by batteries, not shown, although it will be apparent that other power supplies could be used. One particular advantage in the use of batteries is that the variation of the battery output due to temperature is directly proportional to the variation of the test element output due to temperature. Thus, in the calibration procedure, described below, no compensation for temperature is necessary. Warm-up time for the analyzer is less than fifteen seconds.

Figure 12:
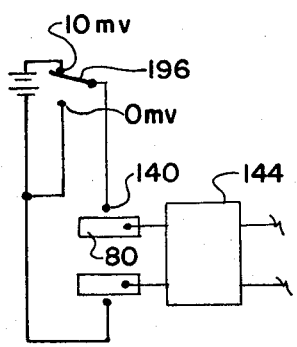
FIG. 12 is a schematic diagram of the electrical circuit for calibration of the analyzer.

Before starting calibration of analyzer 20, the analyzer is set for a particular analyte by means of control 173 (FIGS. 4 and 9). Calibration, in the analog mode, is accomplished by establishing two voltage conditions at the input of electrometer 144 (e.g., 0 mv and 10 mv). Voltage is supplied to probes 80, during calibration, through stop rods 140. (See FIGS. 7, 8, and 12.) The probes 80 are held in contact with rods 140 by means of arm 130. The two voltage conditions are effected through switch 196 on analyzer 20 (FIGS. 4 and 12). In the first step of the calibration procedure, switch 196 is moved to a first position in which the probes 80 are shorted to establish a zero voltage condition at the input of electrometer 144. With the zero voltage condition existing at the input of electrometer 144, potentiometer 163 (FIGS. 4 and 9) is adjusted until the digital voltmeter 170 displays a concentration equal to $k_1$ (the intercept) related to the concentration of the reference fluid. This indicates a matched fluid condition in which the concentration of the sample fluid is equivalent to that of the reference fluid; thus, the response from the test element should be 0 mv. To calibrate the instrument for $K_2$ (the slope), switch 196 is moved to a second position to apply a 10 mv signal to the electrometer 144, and potentiometer 151 is adjusted to obtain a concentration reading on voltmeter 170 equivalent to the concentration of a sample known to produce the 10 mv response. The concentrations equivalent to $K_1$ (concentration of reference fluid) and $K_2$ (concentration to produce a 10 mv response) must be provided to the operator. The stability of the analyzer is such that it can operate for more than eight hours, without requiring further calibration. Calibration of analyzer 20 can also be accomplished through the use of a sample fluid of known concentration. However, because of the necessity of the disclosed device to be compact, portable, and usable under emergency conditions, it is not practical to utilize calibrator fluids.

Calibration of the analyzer in the digital mode (FIG. 10) is generally similar to the procedure described above for the analog mode. The two voltage conditions are established at the input of the electrometer 144, and values for $K_1$ (the intercept) and $K_2$ (slope) are provided to computer 200 through keyboard 204. The values are stored in the computer and are used to convert a measured potential into units of analyte concentration.

In operation of analyzer 20, one of the syringes 54 is charged with a reference fluid which contains known ion concentrations of each of the analytes. Sample fluid is aspirated into tip 64 of the other syringe. Both syringes are placed in holder 56 and mounted on analyzer 20.

When the metering device 24 is ready for operation, a test element for the selected analyte, e.g. $Na^\oplus$, is placed in the receiving position on track 40. The element 30 is moved along track 40 by transfer mechanism 28, until the element abuts against stop 50. T-bar 74 is then actuated to substantially simultaneously deposit reference fluid and sample fluid on element 30. The timing means is actuated, and element 30 is moved into sensing device 26. When alarm 188 in the timing means signals completion of the incubation period, a final reading in units of analyte concentrations is taken from voltmeter 170.

From the foregoing, it will be apparent that applicants have disclosed a compact, portable analyzer that is particularly suitable for use under a variety of operating conditions. An important feature of the disclosed apparatus is the arrangement of the analyzer components such that a test element is processed with a minimum of agitation of the fluids carried by the element. The element 30 is supported in track 40 throughout the entire test procedure to insure dynamic stability of the fluids on the test element. In devices where the test element is transferred from one support means to another, agitation of the fluids can reach a point where the response from the element is affected. The disclosed metering device can be moved to a source of fluid where it aspirates in the desired amount. The analysis device can be electronically calibrated, and thus, no calibrator fluids are necessary. The metering and analysis devices cooperate with the test element support and transfer means to produce a desired analytical result with a minimum of equipment and of operator expertise.

The invention has been described in detail with particular reference to preferred embodiments thereof, but it will be understood that variations and modifications can be effected within the spirit and scope of the invention.

What is claimed is:

1. A portable analytical device for measuring the activity of ions in a biological fluid wherein a plurality of operations are performed on a test element containing a pair of ion-selective electrodes, said device comprising:

track means for receiving a test element from a supply thereof and for supporting the element during each of said operations, said track means providing continuous bearing surface on which the element is moved through the device;

housing means for supporting said track means in a fixed position relative to said test element;

metering means operable in a first location adjacent said track means for substantially simultaneously depositing a predetermined quantity of reference fluid on one electrode and a predetermined quantity of sample fluid on the other electrode of a test element supported in a metering position on said surface, said metering means being operable at a second location to aspirate fluid into said metering means and movable between said locations;

analysis means for measuring an electrical potential developed in a test element bearing said fluids and supported on said track means in a sensing position, said analysis means comprising contact means supported for pivotal movement over said track means;

transfer means for advancing said test element through said device, said transfer means comprising an elongate member mounted for reciprocative movement in said track means, said elongate member being manually actuatable for advancing a test element from said metering position to said sensing position and for effecting the removal of said element from the sensing position after the potential has been measured; and means for pivotally moving said contact means and a test element supported in said sensing position relative to each other to effect an electrical connection between the contact means and said electrodes.

2. A portable analytical device, as defined in claim 1, wherein said pivotally moving means comprises means for biasing said contact means toward said track means and means for lifting said contact means against said biasing means.

3. A portable analytical device, as defined in claim 1, wherein said metering means comprises a pair of dispensing means, and one of said dispensing means is operable independently of the other for aspirating fluid into said metering means.

4. A portable analytical device, as defined in claim 3, wherein mounting means on said device is adapted to removably receive said dispensing means, and said mounting means is adapted to receive said dispensing means in a first position when an ion of one polarity is being tested and in a second position when a ion of a different polarity is being tested.

* * * * *